United States Patent
Wang et al.

(10) Patent No.: US 12,378,582 B2
(45) Date of Patent: Aug. 5, 2025

(54) ENZYMATIC SYNTHESIS METHOD OF 1-PALMITIC ACID-2-OLEIC ACID-3-TRIGLYCERIDE STEARATE

(71) Applicant: Jiangnan University, Wuxi (CN)

(72) Inventors: Xiaosan Wang, Wuxi (CN); Ye Huang, Wuxi (CN); Yifan Wang, Wuxi (CN); Keying Liu, Wuxi (CN); Ye Chen, Wuxi (CN)

(73) Assignee: Jiangnan University, Wuxi (CN)

( * ) Notice: Subject to any disclaimer, the term of this patent is extended or adjusted under 35 U.S.C. 154(b) by 277 days.

(21) Appl. No.: 17/881,644

(22) Filed: Aug. 5, 2022

(65) Prior Publication Data
US 2023/0227870 A1    Jul. 20, 2023

(30) Foreign Application Priority Data
Jan. 19, 2022   (CN) .......................... 202210060924.5

(51) Int. Cl.
*C12P 7/6454*        (2022.01)
*C12N 9/18*           (2006.01)

(52) U.S. Cl.
CPC .............. *C12P 7/6454* (2013.01); *C12N 9/18* (2013.01); *C12Y 301/01003* (2013.01)

(58) Field of Classification Search
CPC ..... C12P 7/6454; C12P 7/6436; C12P 7/6445; C12N 9/18; C12Y 301/01003; A23D 9/04
See application file for complete search history.

(56) References Cited

PUBLICATIONS

Mohamed, I.O., Lipase-Catalyzed Acidolysis of Palm Mid Fraction Oil with Palmitic and Stearic Fatty Acid Mixture for Production of Cocoa Butter Equivalent. 2013, Appl Biochem Biotechnol 171, 655-666 (Year: 2013).*

Zapesochnaya et al., Research in the field of lipids. XV. Synthesis of some cocoa bean butter triglycerides, Zhurnal Obshchei Khimii (1962), 32, 3901-6. (Year: 1962) English translation also included.*

National Center for Biotechnology Information, PubChem Compound Summary for CID 11366450, 1-Palmitoyl-2-oleoyl-3-stearoylglycerol. (Year: 2024).*

National Center for Biotechnology Information. PubChem Compound Summary for CID 6440177, 1-Palmitoyl-2-oleoyl-rac-glycerol. (Year: 2024).*

Xu et al., Enzymatic hydrolysis of palm stearin to produce diacylglycerol with a highly thermostable lipase (2013) Eur. J. Lipid Sci. Technol., 115: 564-570. (Year: 2013).*

Undurraga et al., Cocoa butter equivalent through enzymatic interesterification of palm oil midfraction, Process Biochemistry, vol. 36 , 2001, p. 933-939 (Year: 2001).*

* cited by examiner

*Primary Examiner* — Robert B Mondesi
*Assistant Examiner* — Naghmeh Nina Moazzami
(74) *Attorney, Agent, or Firm* — IDEA Intellectual Limited; Sam T. Yip

(57) ABSTRACT

The present invention discloses an enzymatic synthesis method of 1-palmitic acid-2-oleic acid-3-triglyceride stearate, belonging to the technical field of structured lipid processing. In the present invention, a crude product rich in 1-palmitic acid-2-oleic acid-3-triglyceride stearate is obtained by reacting for 2-10 h at 20-70° C. with 1-palmitic acid-2-diglyceride oleate as an acyl acceptor, stearic acid or a derivative thereof as an acyl donor and a lipase as a catalyst, wherein the reaction system is an inorganic or organic solvent reaction system. The present invention provides a highly efficient enzymatic synthesis method of POS, thereby resolving the disadvantage of low POS content and limited use provided by the current synthesizing product of structured lipid. The technology adopted by the present invention certainly has an application prospect in the process of preparing cocoa butter equivalents.

5 Claims, No Drawings

ENZYMATIC SYNTHESIS METHOD OF 1-PALMITIC ACID-2-OLEIC ACID-3-TRIGLYCERIDE STEARATE

FIELD OF THE INVENTION

The present invention generally relates to the technical field of food processing.

More specifically, the present invention relates to a preparation method of a functional lipid, and it particularly relates to an enzymatic synthesis method of 1-palmitic acid-2-oleic acid-3-triglyceride stearate.

BACKGROUND OF THE INVENTION

Cocoa butter is derived from cocoa trees, which is one of the major raw materials for preparing chocolates. The cocoa trees have relatively high requirements on growing environments and climate conditions. Originated from central and southern America, cocoa trees are widely cultivated in tropical regions all over the world, whereas some regions are not suitable for planting Under the condition of inadequate climate as well as pests and diseases, the global yield of cocoa butter would be sharply declined, which makes the price of natural cocoa butter become very expensive. Therefore, it is extremely important to use cheap raw materials in preparing the triglycerides of cocoa butter.

Main triglycerides in the cocoa butter are 1,3-dipalmitic acid-2-triglyceride oleate (POP), 1-palmitic acid-2-oleic acid-3-triglyceride stearate (POS) and 1,3-dipalmitic acid-2-triglyceride oleate (SOS). They account for nearly 80% of the coca butter, and therefore the objective of preparing artificial cocoa butter equivalents is to obtain these three triglycerides. Some raw materials of natural oil are rich in POP, for example a melting point extract in palm oil; whereas, other natural oils are rich in SOS, for example shea butter. However, there are very few of natural oils rich in POS. Thus, the key to obtaining cocoa butter equivalents, in which compositions are similar to those of cocoa butter, is how to prepare POS.

Currently, a main method for artificially preparing POS is enzymatic acidolysis, that is, a structured lipid rich in POS is prepared by performing enzymatic reaction on a triglyceride rich in POP and stearic acid or methyl stearate or ethyl stearate. However, the product obtained by this method contains multiple triglycerides including not only POS but also POP and SOS, and the product has a relatively low content of POS after molecular distillation.

Therefore, there is still a need for an enzymatic synthesis method of POS to improve synthesis efficiency and increase the content of POS in a crude product.

SUMMARY OF THE INVENTION

In view of the technical problems existing in the above and/or existing method for preparing POS by an enzymatic process, the present invention is proposed.

The present invention provides a method for preparing POS by an enzymatic process, in which POS is synthesized by using a lipase as a catalyst and 1-palmitic acid-2-diglyceride oleate and stearic acid (or derivatives thereof) as reactants. Compared with a method of using enzymatic acidolysis for preparing POS, the method adopted in the present invention has high synthesis efficiency, bringing high POS content in the crude product.

Specifically, the present invention provides the following technical solution: an enzymatic synthesis method of POS, the method comprising: reacting for 2-10 h at 20-70° C. by using 1-palmitic acid-2-diglyceride oleate as an acyl acceptor, stearic acid or a derivative thereof as an acyl donor, and a lipase as a catalyst to obtain a crude product rich in 1-palmitic acid-2-oleic acid-3-triglyceride stearate, wherein the reaction system is an inorganic solvent or organic solvent reaction system.

In one embodiment, the lipase comprises any one or more of lipases derived from *Candidaantarctica, Rhizomucor miehei, Burkaholderia cepacia* and *Rhizopus oryzae*.

In another embodiment, the lipase comprises Novozym 435 derived from *Candidaantarctica*, Lipozyme RM IM derived from *Rhizomucor miehei*, Lipase PS derived from *Burkaholderia cepacia* and Lipase DF IM derived from *Rhizopus oryzae*.

In another embodiment, the organic solvent in the reaction system for enzymatic synthesis of POS is a non-polar organic solvent, including one or more of hexane, petroleum ether, dichloromethane and the like.

In another embodiment, the 1-palmitic acid-2-diglyceride oleate is prepared by enzymatic hydrolysis or alcoholysis of a palm oil extract.

In another embodiment, the lipase used for enzymatic alcoholysis comprises one or more of lipases derived from *Thermomyces lanuginosus* or *Candidaantarctica*, and the lipase used for enzymatic hydrolysis comprises one or more of lipases derived from *Rhizopus oryzae* or *Thermomyces lanuginosus*.

In another embodiment, the lipase used for enzymatic alcoholysis comprises one or more of Lipase CL "Amano" IM, Lipozyme TL IM, Lipase TL 100L and Lipozyme TL 100L.

In another embodiment, the lipase used for enzymatic hydrolysis comprises Lipozyme TL 100L and Lipozyme TL IM derived from *Thermomyces lanuginosus* and Lipase DF IM derived from *Rhizopus oryzae*.

In another embodiment, the reaction conditions for preparing 1-palmitic acid diglyceride oleate by enzymatic hydrolysis or alcoholysis are as follows: the reaction temperature is 25-50° C., and the reaction time is 2-10 h.

In another embodiment, the reaction conditions for preparing 1-palmitic acid-2-diglyceride oleate by enzymatic alcoholysis are as follows: a molar ratio of the reaction substrate palm oil extract to ethanol is 1:60-1:10; a ratio of the palm oil extract to the organic solvent (except the reaction substrate ethanol) is 1:3=1:0.5 (w/v, g/mL).

In another embodiment, the reaction conditions for preparing 1,2-diglyceride by enzymatic alcoholysis are as follows: the organic solvent comprises a solvent formed by mixing one or more of ethanol, dichloromethane, chloroform and acetone.

In another embodiment, the water activity of the enzymatic alcoholysis reaction system is 0.1-0.55, preferably 0.3-0.55.

In one or more embodiments, the additional amount of water in the enzymatic hydrolysis reaction system is 5% or more of the weight of the palm oil extract.

The present invention also provides use of the above preparation method in preparing cocoa butter equivalents.

The beneficial effect is provided by the present invention:

According to the present invention, POS is prepared by using 1-palmitic acid-2-diglyceride oleate or an oil rich in 1-palmitic acid-2-diglyceride oleate as an acyl acceptor and stearic acid or a derivative thereof as an acryl donor in the presence of a lipase, the enzymatic reaction product contains a few of other types of triglycerides and has relatively high POS content, and therefore the preparation efficiency of POS can be improved.

DETAILED DESCRIPTION

Next, the present invention will be further described in combination with examples, but embodiments of the present invention are not limited thereto.

For making the above objective, features and advantages of the present invention more clear, specific embodiments of the present invention will be described in detail with specific examples below.

The following descriptions set forth many details to be convenient for sufficiently understanding the present invention, however, the present invention can also be implemented in other modes different from the descriptions. A person skilled in the art can make similar promotions without violating the connotation of the present invention, so the present invention is not limited by the specific embodiments disclosed below.

Next, the phase "one embodiment" or "embodiment" here refers to comprising specific features, structures or characteristics of at least one implementation mode of the present invention. "One embodiment" occurring in different places of the specification does not refer to the same embodiment, nor do they individually or selectively exclude other embodiments.

Detection Method

Detection method of a diglyceride: a method that refers to Zhang Yu's Doctoral Dissertation (Comparative study on preparation and purification of DHA and 2-DHA-monoglyceride and regulation of lipid metabolism in HepG2 cells).

Detection method of POS: a method that refers to Jin Jun's Doctoral Dissertation (Preparation of mango kernel oil-based heat-resistant chocolate oil and study on its frost resistance).

Calculation method of the diglyceride yield: a ratio of the weight of an actually obtained diglyceride (or POS) to the weight of a theoretically obtained diglyceride (or POS).

I. Preparation of 1,2-Diglyceride by Enzymatic Alcoholysis

Example 1: (Selection of Solvent Types)

2.0 mmol of intermediate hard palm oil extract was melted and then mixed with 80 mmol of absolute ethyl alcohol, 2 mL of organic solvent was added, the water activity of a reaction system was adjusted to 0.53, and the lipase Lipozyme TL IM (derived from *Thermomyces lanuginosus*) was subsequently added in an addition amount (relative to a mass fraction of oil) of 8% to perform enzymatic reaction for 7 h at 30° C. under the magnetic stirring condition of 300 r/min. The lipase was removed by centrifugation after the reaction was ended, supernatant was taken, compositions of a lipid in a crude reaction product were detected, and the yield of 1,2-diglyceride was calculated. Results are as shown in Table 1.

It can be seen from Table 1 that when acetone, chloroform or dichloromethane is added as an organic solvent of an alcoholysis reaction system, relatively high 1,2-diglyceride yields are obtained, especially when acetone is added, the yield of 1,2-diglyceride in the reaction system is maximum, reaching 65.8%, which is significantly improved by 21.2% compared with that when ethanol is used alone (the yield of 1,2-diglyceride is 54.3%). When other solvents are added, for example n-hexane and tertiary butanol are used as reaction solvents, the yield of 1,2-diglyceride is obviously relatively low. As can be seen, different reaction solvents can affect the yield of 1,2-diglyceride prepared by enzymatic alcoholysis. Therefore, the organic solvents are preferably acetone, chloroform, dichloromethane and ethanol.

TABLE 1

Influence of different types of organic solvents on the yield of 1,2-diglyceride in alcoholysis reaction

| 2 mL of solvent | Acetone | Chloroform | Dichloromethane | Ethanol | n-hexane | Tertbutanol |
|---|---|---|---|---|---|---|
| Yield of 1,2-diglyceride | 65.8% | 53.8% | 58.1% | 54.3% | 25.6% | 13.2% |

Example 2: (Addition Amount of Solvent)

2.0 mmol of intermediate hard palm oil extract was melted and then mixed with 80 mmol of absolute ethyl alcohol, a certain amount of acetone was added as an organic solvent, the water activity of a reaction system was adjusted to 0.53, and the lipase Lipozyme TL 100L (derived from *Thermomyces lanuginosus*) was subsequently added in an addition amount (relative to a mass fraction of oil) of 4% to perform enzymatic reaction for 8 h at 30° C. under the magnetic stirring condition of 300 r/min. The lipase was removed by centrifugation after the reaction was ended, supernatant was taken, compositions of a lipid in a crude reaction product were detected, and the yield of 1,2-diglyceride was calculated. Results are as shown in Table 2.

TABLE 2

Influence of addition amount of acetone on the yield of 1,2-diglyceride in alcoholysis reaction

| | Additional amount of acetone | | |
|---|---|---|---|
| | 1 mL | 2 mL | 3 mL |
| Yield of 1,2-diglyceride | 62.7% | 65.2% | 64.8% |

Example 3: (Water Activity)

2.0 mmol of intermediate hard palm oil extract was melted and then mixed with 80 mmol of absolute ethyl alcohol, 2 mL of acetone was added as an organic solvent, the water activity of a reaction system was adjusted with different saturated hydrochloric acid solutions, and the Lipase CL "Amano" IM (derived from *Candidaantarctica*) was subsequently added in an addition amount (relative to a mass fraction of oil) of 10% to perform enzymatic reaction for 7 h at 35° C. under the magnetic stirring condition of 300 r/min. The lipase was removed by centrifugation after the reaction was ended, supernatant was taken, compositions of a lipid in a crude reaction product were detected, and the yield of 1,2-diglyceride was calculated. Results are as shown in Table 3. As can be seen, different water activities obviously affect the yield of 1,2-diglyceride, and too-high water activity can significantly reduce the yield of 1,2-diglyceride.

TABLE 3

Influence of different water activities on the yield of 1,2-diglyceride in alcoholysis reaction

| | Water activity | | | | |
|---|---|---|---|---|---|
| | 0.11 | 0.33 | 0.43 | 0.53 | 0.97 (comparative example 3) |
| Yield of 1,2-diglyceride | 47.6% | 57.7% | 60.9% | 63.1% | 38.5% |

Example 4: (Molar Ratio of Substrate)

2.0 mmol of intermediate hard palm oil extract was melted and then mixed with a certain amount of absolute ethyl alcohol, 2 mL of acetone was added as an organic solvent, the water activity of a reaction system was adjusted to 0.53 with a saturated hydrochloric acid solution, and a lipase Lipozyme TL IM (derived from *Thermomyces lanuginosus*) was subsequently added in an addition amount (relative to a mass fraction of oil) of 6% to perform enzymatic reaction for 3 h at 45° C. under the magnetic stirring condition of 300 r/min. The lipase was removed by centrifugation after the reaction was ended, supernatant was taken, compositions of a lipid in a crude reaction product were detected, and the yield of 1,2-diglyceride was calculated. Results are as shown in Table 4.

TABLE 4

Influence of different substrate molar ratios on the yield of 1,2-diglyceride in alcoholysis reaction

| | Intermediate hard palm oil extract:ethanol (molar ratio) | | | |
|---|---|---|---|---|
| | 1:60 | 1:50 | 1:40 | 1:20 |
| Yield of 1,2-diglyceride | 49.6% | 57.8% | 59.5% | 56.9% |

Example 5: (Types of Enzymes)

2.0 mmol of intermediate hard palm oil extract was melted and then mixed with 80 mmol of absolute ethyl alcohol, 2 mL of acetone was added as an organic solvent, the water activity of a reaction system was adjusted to 0.53 with a saturated hydrochloric acid solution, and lipases from different sources were subsequently added in an addition amount (relative to a mass fraction of oil) of 6% to perform enzymatic reaction for 8 h at 30° C. under the magnetic stirring condition of 300 r/min. The lipases were removed by centrifugation after the reaction was ended, supernatant was taken, compositions of a lipid in a crude reaction product were detected, and the yield of 1,2-diglyceride was calculated. Results are as shown in Table 5.

TABLE 5

Influence of different types of enzymes on the yield of 1,2-diglyceride in alcoholysis reaction

| Types of enzymes | Lipase TL 100L | Lipase CL "Amano" IM | Lipozyme DF IM (comparative example) | Lipozyme RM IM (comparative example) | Lipase AY 400SD (comparative example) | NS 40086 (comparative example) |
|---|---|---|---|---|---|---|
| Yield of 1,2-diglyceride | 64.1% | 55.4% | 0 | 2.7% | 0 | 0 |

II. Preparation of Diglyceride by Enzymatic Hydrolysis

Example 6: (Addition Amount of Water)

10.0 g of melted intermediate soft palm oil extract sample was weighed, a different amount of water was added into an enzymatic reactor, 5% (w/w, enzyme/oil) of Lipozyme TL IM lipase (derived from *Thermomyces lanuginosus*) was subsequently added, and the above materials reacted for 4 h under the condition of magnetic stirring at a reaction temperature of 35° C. After the reaction was ended, water and the lipase were removed by centrifugation to obtain a mixture rich in diglyceride. Results are as shown in Table 6.

TABLE 6

Influence of different water contents on the yield of diglyceride

| | Addition amount of water | | | | |
|---|---|---|---|---|---|
| | 5% | 9% | 20% | 30% | 2% (comparative example) |
| Yield of 1,2-diglyceride | 42.6% | 51.8% | 49.5% | 48.7% | 25.3% |

Example 7: (Temperature and Time)

10.0 g of melted intermediate soft palm oil extract sample was weighed, 9% of water was added into an enzymatic hydrolysis reaction system, 2% (enzyme/oil, w/w) of Lipozyme TL 100L lipase (derived from *Thermomyces lanuginosus*) was subsequently added, and the above materials reacted for a while under the condition of magnetic stirring at a certain reaction temperature. After the reaction was ended, water and the lipase were removed by centrifugation to obtain a mixture rich in 1,2-diglyceride. Results are as shown in Table 7.

TABLE 7

Influences of different temperatures and times on the yield of 1,2-diglyceride

| | Temperature or time | | | | | | | | | |
|---|---|---|---|---|---|---|---|---|---|---|
| | 35° C. | | | 40° C. | | | 50° C. | | | 25° C. (comparative example) |
| | 2 h | 5 h | 8 h | 2 h | 5 h | 8 h | 2 h | 5 h | 8 h | 2 h |
| Yield of 1,2-diglyceride | 52.5% | 51.0% | 47.8% | 50.2% | 48.6% | 44.9% | 48.8% | 46.4% | 43.1% | 18.5% |

Example 8: (Types of Enzymes)

10.0 g of melted intermediate soft palm oil extract sample was weighed, 9% of water was added into an enzymatic hydrolysis reaction system, and 5% (w/w, enzyme/oil) of lipases from different sources, namely, Lipozyme TL IM (derived from *Thermomyces lanuginosus*), Lipase DF IM (derived from *Rhizopus oryzea*), Lipase AY "Amano" 30SD (derived from Candiacylindreacea), Lopozyme RM IM (derived from *Rhizomucor miehei*), were subsequently and respectively added. The above materials reacted for 4 h under the condition of magnetic stirring at a reaction temperature of 35° C. After the reaction was ended, water and the lipase were removed by centrifugation to obtain a mixture rich in 1,2-diglyceride. Results are as shown in Table 8.

TABLE 8

Influence of lipases on the yield of 1,2-diglyceride in enzymatic reaction system

| | Lipases | | | |
|---|---|---|---|---|
| | Lipozyme TL IM | Lipase DF IM | Lipase AY "Amano" 30SD (comparative example) | Lipozyme TL IM (comparative example) |
| Yield of 1,2-diglyceride | 51.8% | 55.4% | 6.5% | 11.6% |

The mixture rich in 1,2-diglyceride obtained in examples 1-8 was purified to high-purity 1,2-diglycerides. The purification methods include solvent extraction and crystallization. That is, 10 g of crude product rich in 1,2-diglyceride was sufficiently mixed with n-hexane (30 mL-60 mL) and then crystallized at −4° C. to −10° C., the obtained mixture was shaken when a large amount of crystals are generated, and a white crystal rich in 1,2-diglyceride was obtained by filtration; subsequently, the obtained 1,2-diglyceride crystal was mixed with 15 mL of 95% acetonitrile aqueous solution or 84% ethanol aqueous solution at room temperature, 15 mL of n-hexane was added for extraction, and a layer of n-hexane was collected after layering, so as to finally obtain 1,2-diglyceride having a content of more than 95%.

III. Preparation of 1-palmitic acid-2-oleic acid-3-triglyceride stearate (POS) by Enzymatic Process

Example 9: (Reaction Temperature)

Under the conditions of example 1, 1,2-diglyceride was prepared by enzymatic alcoholysis based on an intermediate hard palm oil extract as a substrate and 2 mL of acetone as a reaction solvent, and the crude product obtained after the reaction was subjected to solvent crystallization and purified by an extraction method to obtain 1,2-diglyceride having a purity of more than 95%, wherein the highest content of 1,2-diglyceride is 1-palmitic acid-2-diglyceride oleate.

2 mmol of 1,2-diglyceride prepared and purified under the above conditions was weighed, 2.2 mmol of vinyl stearate was added, then 6% of Novozym 435 lipase (derived from *Candidaantarctica*) as a catalyst and 1 mL of dichloromethane were was subsequently added, and the above reaction mixture reacted for a while at a certain temperature. After the reaction, unreacted vinyl stearate and metaglyceride were removed by molecular distillation (a distillation temperature was 180° C., and a pressure was 2 Pa), and the contents of triglyceride and POS type triglyceride in the crude product were analyzed. Results are as shown in Table 9.

TABLE 9

Influence of different reaction temperatures and times on the content of POS in a product after molecular distillation

| | Temperature or time | | | | | | | | |
|---|---|---|---|---|---|---|---|---|---|
| | 20° C. | | | 40° C. | | | 60° C. | | |
| | 2 h | 5 h | 8 h | 2 h | 5 h | 8 h | 2 h | 5 h | 8 h |
| The content of POS in a product after molecular distillation | 40.2% | 45.7% | 45.9% | 41.8% | 46.0% | 45.6% | 43.8% | 41.2% | 39.6% |

It can be seen Table 9 that at different reaction temperatures and times, the contents of triglycerides in the purified product after molecular distillation are all more than 97%, wherein the content of 1-palmitic acid-2-oleic acid-3-triglyceride stearate (POS) is about 40%. In the currently found natural oils, the content of POS in other natural oils is generally no more than 10%, except cocoa butter is rich in about 40% of POS.

Example 10: (Reaction System)

Under the conditions of example 1, 1,2-diglyceride was prepared by enzymatic alcoholysis based on an intermediate hard palm oil extract as a substrate and 2 mL of acetone as a reaction solvent, the crude product after the reaction was subjected to solvent crystallization and purified by an extraction method to obtain 1,2-diglyceride having a purity of more than 95%.

2 mmol of 1,2-diglyceride prepared and purified under the above conditions was weighed, 4 mmol of vinyl stearate was added, then 8% of Lipase DF IM (derived from *Rhizopus oryzea*) was added as a catalyst, 1 mL of organic solvent was added or not added in the reaction system, and the above reaction mixture reacted for 7 h at 60° C. After the reaction, unreacted vinyl stearate and metaglyceride were removed by molecular distillation (a distillation temperature was 185° C., and a pressure was 1 Pa), and the contents of triglyceride and POS type triglyceride in the crude product were analyzed. Results are as shown in Table 10. After the crude reaction product was distilled, the content of triglyceride in the purified product was more than 93%, wherein the content of POS in triglyceride was more than 47%.

TABLE 10

Influence of reaction system on the content of POS in a product after molecular distillation

| | Reaction system | | | |
|---|---|---|---|---|
| | No solvent | Dichloromethane | n-hexane | Ether |
| The content of POS in a product after molecular distillation | 52.4% | 47.3% | 56.8% | 55.1% |

Example 11: (Pressure of Reaction System)

Under the conditions of example 8, 1,2-diglyceride was prepared by enzymatic alcoholysis based on an intermediate hard palm oil extract as a substrate and Lipase DF IM as a hydrolase, and the crude product obtained after the reaction was subjected to solvent crystallization and purified by an extraction method to obtain 1,2-diglyceride having a purity of more than 95%.

2 mmol of 1,2-diglyceride prepared and purified under the above conditions was weighed, 3 mmol of vinyl stearate was added, then 8% of Lipase DF IM (derived from *Rhizopus oryzea*) was added as a catalyst, an organic solvent was not added in the reaction system, and the above reaction mixture reacted for 7 h at 60° C. under a certain pressure. After the reaction, unreacted vinyl stearate and metaglyceride were removed by molecular distillation (a distillation temperature was 175° C., and a pressure was 0.8 Pa), and the contents of triglyceride and POS type triglyceride in the crude product were analyzed. Results are as shown in Table 11.

After the crude reaction product was distilled, the content of triglyceride in the purified products was more than 93%, wherein the content of POS in triglyceride was more than 50%. When the enzymatic reaction was performed under a certain vacuum degree, the content of POS in the purified product was higher.

TABLE 11

Influence of pressure of reaction system on the content of POS in a product after molecular distillation

| | Pressure in the reaction system | | | |
|---|---|---|---|---|
| | Normal pressure | 100 Pa | 300 Pa | 500 Pa |
| The content of POS in a product after molecular distillation | 51.9% | 59.5% | 57.9% | 57.2% |

Example 12: (Types of Lipases)

Under the condition of example 8, 1,2-diglyceride was prepared by enzymatic hydrolysis based on an intermediate hard palm oil extract as a substrate and Lipase DF IM as a hydrolase, the crude product after the reaction was subjected to solvent crystallization and purified by an extraction method to obtain 1,2-diglyceride having a purity of more than 95%.

2 mmol of 1,2-diglyceride prepared and purified under the above conditions was weighed, 3 mmol of stearic acid was added, then 10% of lipases from different sources as catalysts, including Lipase DF IM derived from *Rhizopus oryzea*, Lipozyme RM IM derived from *Rhizomucor miehei*, Lipase PS derived from *Burkaholderia cepacia*, Lipozyme TL IM derived from *Thermomyces lanuginosus* and Lipase AY 30SD derived from Candidacylindracea, an organic solvent was not added in the reaction system, and the above reaction mixture reacted for 7 h at 60° C. under 300 Pa. After the reaction, unreacted stearic acid and metaglyceride were removed by molecular distillation (a distillation temperature was 185° C., and a pressure was 3 Pa), and the contents of triglyceride and POS type triglyceride in the crude product were analyzed. Results are as shown in Table 12.

After the crude reaction product was distilled, the content of POS in triglyceride in experiment group was more than 43%. In control groups using Lipozyme TL IM and Lipase AY 30SD as catalysts, the content of POS in the product was no more than 26%.

TABLE 12

Influence of types of lipases on the content of POS in a product after molecular distillation

| | Types of lipases | | | | |
|---|---|---|---|---|---|
| | Lipase DF IM | Lipase RM IM | Lipase PS | Lipozyme TL IM (comparative example) | Lipozyme AY 30SD (comparative example) |
| The content of POS in a product after molecular distillation | 57.5% | 52.7% | 43.8% | 26.0% | 17.8% |

Example 13: (Preparation of 1,2-Diglyceride by Using Different Oils)

Under the conditions of example 8, 1,2-diglyceride was prepared by enzymatic hydrolysis based on an intermediate hard palm oil extract, soybean oil and peanut oil as substrates and Lipase DF IM as a hydrolase, the crude product after the reaction was subjected to solvent crystallization and purified by an extraction method to obtain 1,2-diglyceride having a purity of more than 95%.

2 mmol of 1,2-diglyceride prepared and purified under the above conditions was weighed, 4 mmol of stearic acid was added, then 10% of lipase DF IM (derived from *Rhizopus oryzae*) was added as a catalyst, an organic solvent was not added in the reaction system, and the above reaction mixture reacted for 7 h at 60° C. under the pressure of 300 Pa. After the reaction, unreacted stearic acid and metaglyceride were removed by molecular distillation (a distillation temperature was 185° C., and a pressure was 3 Pa), and the contents of triglyceride and POS type triglyceride in the crude product were analyzed. Results are as shown in Table 13.

After the crude reaction product was distilled, the content of triglyceride in the purified product was more than 96%, the content of POS in triglyceride in experiment group was more than 55%. When Lipozyme TL IM and Lipase AY 30SD were used as catalysts, the content of POS in the product was no more than 10%.

TABLE 13

Influence of types of oils on the content of POS in a product after molecular distillation

| | Types of oils | | |
|---|---|---|---|
| | Intermediate hard palm oil extract | Soybean oil (comparative example) | Peanut oil (comparative example) |
| The content of POS in a product after molecular distillation | 57.6% | 5.7% | 6.2% |

Example 14: (1,2-Diglyceride from Different Sources)

Under the conditions of example 1, 1,2-diglyceride was prepared by enzymatic alcoholysis based on an intermediate hard palm oil extract as a substrate and 2 mL of acetone as a reaction solvent, the crude product after the reaction was subjected to solvent crystallization and purified by an extraction method to obtain 1,2-diglyceride having a purity of more than 95%. The 1,2-diglyceride synthesized by using the intermediate hard palm oil extract as a raw material or commercially available 1-palmitic acid-2-diglyceride oleate was used as a reaction substrate to synthesize POS.

2 mmol of 1,2-diglyceride synthesized under the above conditions and 2 mmol of commercially available 1-palmitic acid-2-diglyceride oleate were respectively weighed, 2.2 mmol of vinyl stearate was added, then 6% of Novozym 435 lipase (derived from *Candidaantarctica*) as a catalyst and 1 mL of dichloromethane were added, and the above reaction mixture reacted for 5 h at 40° C. After the reaction, unreacted vinyl stearate and metaglyceride were removed by molecular distillation (a distillation temperature was 180° C., and a pressure was 2 Pa), and the contents of triglyceride and POS type triglyceride in the crude product were analyzed. Results are as shown in Table 14. It can be seen from the above table that the content of 1-palmitic acid-2-diglyceride oleate in 1,2-diglyceride prepared from natural oils is relatively low. If high-purity 1-palmitic acid-2-diglyceride oleate is used as the substrate to synthesize POS, the higher content of POS can be obtained. However, commercially available pure 1-palmitic acid-2-diglyceride oleate is extremely expansive in price and cannot be supplied in large quantity, and therefore use of commercially available pure 1-palmitic acid-2-diglyceride oleate as the reaction substrate to synthesize POS has small application prospect.

TABLE 14

Influence of 1,2-diglyceride from different sources on the content of POS in a product after molecular distillation

| | Sources of 1,2-diglyceride | |
|---|---|---|
| | Synthesized 1,2-diglyceride | commercially available 1-palmitic acid-2-diglyceride oleate |
| The content of POS in a product after molecular distillation | 46% | 93.4% |

It should be noted that the above examples are only for illustrating the technical solution of the present invention but not limiting. Although the present invention has been described in detail by reference to preferred embodiments, a person of ordinary skill in the art should understand that amendments or equivalent replacements can be made to the technical solution of the present invention without departing the spirit and scope of the technical solution of the present invention, which shall be included within the scope of the appended claims of the present invention.

The invention claimed is:

1. A method for enzymatically synthesizing a 1-palmitic acid-2-oleic acid-3-triglyceride stearate comprises reacting for 2-10 h at 20-70° C. in a solvent-free reaction system, wherein the reaction system comprises:
 a 1-palmitic acid-2-diglyceride oleate acting as an acyl acceptor;
 a stearic acid or a derivative thereof acting as an acyl donor; and
 a lipase acting as a catalyst;
 wherein the lipase is derived from the group consisting of a *Candidaantarctica*, a *Rhizomucor miehei*, a *Burkaholderia cepacia*, a *Rhizopus oryzae*, or any combinations or selections thereof, and the lipase comprises a *Candidaantarctica*-derived Novozym 435, a *Rhizomucor miehei*-derived Lipozyme RM IM, a *Burkaholderia cepacia*-derived Lipase PS, and a *Rhizopus oryzae*-derived Lipasc DF IM.

2. The method of claim 1, comprising, making the 1-palmitic acid-2-diglyceride oleate from a palm oil extract by enzymatic hydrolysis or enzymatic alcoholysis.

3. The method of claim 1, wherein the reaction system comprises making cocoa butter equivalents.

4. The method of claim 2, wherein the lipase for enzymatic alcoholysis is derived from the group consisting of a *Thermomyces lanuginosus*, a *Candidaantarctica*, or any combinations or selections thereof, wherein the lipase for enzymatic hydrolysis is derived from the group selected from a *Rhizopus oryzae*, a *Thermomyces lanuginosus*, or any combinations thereof.

5. The method of claim 2, wherein the reaction temperature for enzymatic hydrolysis or enzymatic alcoholysis is 25-50° C., wherein the reaction time is 2-10 h.

* * * * *